US010473560B2

(12) United States Patent
Nelson et al.

(10) Patent No.: US 10,473,560 B2
(45) Date of Patent: Nov. 12, 2019

(54) PIPE CORE SAMPLING AND TAPPING APPARATUS

(71) Applicant: Hydra-Stop LLC, Burr Ridge, IL (US)

(72) Inventors: Andrew J. Nelson, Chicago, IL (US); Christopher C. Vazzana, Palos Park, IL (US); Carl Mastny, Crete, IL (US)

(73) Assignee: Hydra-Stop LLC, Burr Ridge, IL (US)

( * ) Notice: Subject to any disclaimer, the term of this patent is extended or adjusted under 35 U.S.C. 154(b) by 102 days.

(21) Appl. No.: 15/836,470

(22) Filed: Dec. 8, 2017

(65) Prior Publication Data

US 2019/0178758 A1    Jun. 13, 2019

(51) Int. Cl.
| | | |
|---|---|---|
| *G01N 1/08* | (2006.01) | |
| *F16L 41/06* | (2006.01) | |
| *F16L 47/34* | (2006.01) | |
| *F16L 55/18* | (2006.01) | |
| *B23B 51/04* | (2006.01) | |
| *F16L 55/105* | (2006.01) | |

(52) U.S. Cl.
CPC ............ *G01N 1/08* (2013.01); *B23B 51/0406* (2013.01); *F16L 41/06* (2013.01); *F16L 47/345* (2013.01); *F16L 55/18* (2013.01); *F16L 55/105* (2013.01); *F16L 2201/20* (2013.01)

(58) Field of Classification Search
CPC ........ G01N 1/008; F16L 41/06; F16L 47/345; F16L 55/18; Y10T 137/6123
See application file for complete search history.

(56) References Cited

U.S. PATENT DOCUMENTS

| 485,715 A | * | 11/1892 | Smith | B23B 51/044 |
| | | | | 408/67 |
| 1,045,289 A | * | 11/1912 | Hill | B23B 51/05 |
| | | | | 29/213.1 |
| 2,679,173 A | * | 5/1954 | Hill | F16L 41/04 |
| | | | | 138/89 |
| 2,972,915 A | * | 2/1961 | Milanovits | B23B 51/044 |
| | | | | 137/318 |

(Continued)

OTHER PUBLICATIONS

United Kingdom Search Report for related Application No. GB1817246.0; report dated Apr. 25, 2019.

*Primary Examiner* — Eric Keasel
*Assistant Examiner* — Kevin R Barss
(74) *Attorney, Agent, or Firm* — Miller, Matthias & Hull LLP (57) ABSTRACT

A core sampling and tapping assembly is disclosed that may be mounted to a cylindrical pipe. The assembly includes a nozzle having an interior portion extending between an open distal end and a proximal end. The proximal end sealed to an upper saddle member and the upper saddle member coupled to a lower saddle member to clamp the pipe in between. The assembly further includes a tapping mandrel including a mandrel plate, the tapping mandrel extending through the interior portion and a core cutter fixedly coupled to the mandrel plate. The assembly further includes a pilot bit coupled to the mandrel plate and disposed within an interior cavity of the core cutter. The tapping mandrel adjacently aligns the core cutter and the pilot bit with an outer surface of the pipe and subsequently rotates the pilot bit and core cutter to collect a core sample from the pipe.

28 Claims, 7 Drawing Sheets

(56) References Cited

U.S. PATENT DOCUMENTS

| | | | | |
|---|---|---|---|---|
| 3,995,655 | A | * | 12/1976 | Sands .................. F16L 41/06 137/318 |
| 4,077,737 | A | * | 3/1978 | Morse ............... B23B 51/0426 144/23 |
| 4,350,052 | A | * | 9/1982 | Kendall ................ G01N 1/10 137/318 |
| 4,680,848 | A | * | 7/1987 | Goldner ............... F16L 41/04 137/318 |
| 5,257,644 | A | * | 11/1993 | Saha .................. B26D 7/1836 137/318 |
| 5,660,199 | A | | 8/1997 | Maichel |
| 5,893,686 | A | * | 4/1999 | Weiler ................. F16L 41/06 137/315.42 |
| 5,964,240 | A | * | 10/1999 | Granovski ............ F16L 41/06 137/15.13 |
| 6,126,369 | A | * | 10/2000 | Jiles .................... F16L 41/04 137/318 |
| 6,640,827 | B1 | * | 11/2003 | McClure ............... F16L 41/06 137/318 |
| 6,648,562 | B1 | * | 11/2003 | Calkins ................ F16L 41/04 137/318 |
| 7,357,605 | B2 | | 4/2008 | Weiler |
| 2008/0309072 | A1 | * | 12/2008 | Dole ..................... F16L 41/06 285/197 |
| 2015/0247602 | A1 | | 9/2015 | Vazzana et al. |

\* cited by examiner

PIPE CORE SAMPLING AND TAPPING APPARATUS

TECHNICAL FIELD

This disclosure relates generally to tapping equipment for a pressurized pipe or conduit. More specifically, this disclosure relates to tapping equipment that includes a core sampling apparatus to determine characteristics of the pressurized pipe prior to tapping.

BACKGROUND

Pressurized conduits or pipes convey fluids, both liquid and gas, in municipalities, industrial plants and commercial installations. When originally installed, a network of pipes may include isolation valves used to block or otherwise isolate certain sections of the pipe for repairs, relocation or installation of new components into the pipe. For example, when a shutdown is required in a municipal water system, a significant portion of a supply area may be deprived of water service. Accordingly, in addition to the inconvenience to residents, schools, hospitals, commercial and/or industrial facilities may have to be shut down until water service is restored.

When a network of pipes is in need of repair maintenance crews make every attempt to perform the repairs quickly and with minimal service interruption. However, many municipalities, industrial plants and other commercial installations have incomplete, outdated or inaccurate records for the network of pipes which make it difficult to determine certain pipe characteristics such as but not limited to, size, material, class or other such specification. Exposing the outside of a pipe in need of repair can provide information related to pipe material and pipe outer diameter. However, determination of pipe class and internal pipe geometry may require use of expensive pipe imaging and gauging equipment (e.g., ultrasonic, radiation or other such imaging technology), drilling and tapping multiple holes in the pipe or even removing an entire section of pipe for closer inspection.

Therefore, maintenance crews have a need for alternative technology that provides an efficient and reliable method for determining internal pipe geometries such as but not limited to, wall thickness and internal diameter in order to select the proper tools and replacement parts to carry out pipe network repairs. As a result, equipment which cuts two taps into a single pipe location (e.g., a core sample and a secondary tap) can reduce repair costs, reduce pipe network downtime, and help maintain overall integrity of the pipe.

A hole saw including a pilot drill is disclosed in U.S. Pat. No. 7,357,605 (hereinafter the "'605 patent"), entitled, "Pilot Drill with Coupon Retainer and Hot Tapping Machine Using the same." The tapping device of the '605 patent includes a hand drill to turn a shaft having a hole saw at the inner end thereof to drill a hole and provide a new tap in the pressurized main. The pilot drill has cutting blades and a hole formed through the drill. The hole includes a wire disposed there through and when the pilot drill penetrates the wall of the main the wire ends may sling outward serving as a coupon retaining finger or arms. However, the tapping device of the '605 patent does not first provide a core cutter which may retrieve a core sample to determine unknown characteristics of the main and subsequently provide a size-on-size cutter to form the new tap in the main. Furthermore, the tapping device of the '605 patent is not interchangeable for particular application needs.

Accordingly, improved core sampling and tapping assemblies that may be installed in pressurized pipes and conduits to sample the pipe prior to tapping are needed.

SUMMARY OF THE DISCLOSURE

In one aspect, this application discloses a core sampling and tapping assembly for mounting to a cylindrical pipe. The disclosed core sampling and tapping assembly may include a nozzle having an interior portion extending between an open distal end and a proximal end. In some cases, the proximal end of the nozzle may be sealingly coupled to an upper saddle member and the upper saddle member is coupled to a lower saddle member for clamping the cylindrical pipe there between. The core sampling and tapping assembly may further include a tapping mandrel inserted into the open distal end of the nozzle and extending through the interior portion. The tapping mandrel may further include a mandrel plate attached at a first end of a mandrel shaft and a hex pattern formed at a second end of the mandrel shaft. Furthermore, in an embodiment, a core cutter is fixedly coupled to the mandrel plate and a pilot bit is operably coupled to the mandrel plate and disposed within an interior cavity of the core cutter. The tapping mandrel adjacently aligns the core cutter and the pilot bit with an outer surface location of the cylindrical pipe, and wherein the core sampling and tapping assembly rotatably drives the hex pattern of the tapping mandrel to subsequently rotate the pilot bit and core cutter to collect a core sample from the cylindrical pipe.

In another aspect, this application discloses a core sampling and tapping assembly for mounting to a cylindrical pipe. The core sampling and tapping assembly may include a nozzle having an interior portion extending between an open distal end and a proximal end. The proximal end may be sealingly coupled to an upper saddle member and the upper saddle member is coupled to a lower saddle member for clamping the cylindrical pipe there between. Furthermore, in an embodiment, the interior portion of the nozzle further includes a distal portion having a distal portion inner diameter and a proximal portion having a proximal portion inner diameter that is smaller than the distal portion inner diameter. The core sampling and tapping assembly further includes a tapping mandrel inserted into the open distal end of the nozzle and extending through the interior portion and the tapping mandrel includes a mandrel plate attached at a first end of the mandrel shaft and a hex pattern formed at a second end of the mandrel shaft.

In yet another aspect, this application discloses a core sampling and tapping assembly for mounting to a cylindrical pipe. The core sampling and tapping assembly includes a nozzle having an interior portion extending between an open distal end and a proximal end. The proximal end of the nozzle is sealingly coupled to an upper saddle member and the upper saddle member is coupled to a lower saddle member for clamping the cylindrical pipe there between. In an embodiment, the core sampling and tapping assembly further includes a tapping mandrel inserted into the open distal end of the nozzle and extending through the interior portion. The tapping mandrel further including a mandrel plate attached at a first end of a mandrel shaft and a hex pattern formed at a second end of the mandrel shaft. Furthermore, the core sampling and tapping assembly includes a core sampling and tapping fixture operably coupled to the mandrel plate. The core sampling and tapping fixture includes a core cutter fixedly coupled to the mandrel plate and a pilot bit operably coupled to the mandrel plate and disposed within an interior cavity of the core cutter. The tapping mandrel adjacently aligns the core cutter and the pilot bit with an outer surface location of the cylindrical pipe. Additionally, the core sampling and tapping fixture includes a secondary tap interchangeable with the core cutter and the secondary tap is threaded onto a mandrel component attachment portion of the tapping mandrel and fixedly attached to the mandrel plate. Furthermore, the core sampling and tapping fixture includes a centering tool having a centering tool shaft being inserted through a cutter attachment hole and extending into the mandrel shaft such that the centering tool is fixedly attached to the tapping mandrel.

In any one or more of the embodiments described above, the core sampling and tapping assembly further includes a mandrel adaptor axially disposed between the mandrel plate and the core cutter, wherein the mandrel adaptor includes a threaded portion that correspondingly threads onto a threaded component attachment portion of the tapping mandrel such that the mandrel adaptor is fixedly coupled to the mandrel plate.

In any one or more embodiments described above, the mandrel adaptor further includes a core cutter post and an adaptor bore centered within the core cutter post, and wherein the core cutter is threaded onto the core cutter post to fixedly attach the core cutter to the mandrel adaptor, and wherein the pilot bit is inserted into the adaptor bore and secured to the mandrel adaptor with a set screw.

In any one or more of the embodiments described above, the core sampling and tapping assembly may further include a centering ring having a ring attachment hole, wherein the mandrel shaft extends through the ring attachment hole and the centering ring is fixedly coupled to the mandrel plate.

In any one or more of the embodiments described above, the centering ring further includes one or more equalization holes extending there through, and wherein the one or more equalization holes are positioned outside a diameter of the mandrel plate to allow fluid to travel through the centering ring as the core sampling and tapping assembly is actuated within the nozzle.

In any one or more of the embodiments described above, the centering ring has a diameter smaller than an inner diameter of the nozzle, and wherein a circumference of the centering ring is slidingly and rotatingly engaged with an interior surface of the nozzle and wherein the centering ring centers the tapping mandrel, the core cutter and the pilot bit within the nozzle.

In any one or more of the embodiments described above, the inner diameter of the nozzle includes a distal portion inner diameter and a proximal portion inner diameter that is smaller than the distal portion inner diameter, wherein the diameter of the centering ring is smaller than the distal portion inner diameter and larger than the proximal inner diameter of the interior portion of the nozzle, and wherein the distal portion inner diameter and the proximal inner diameter of the interior portion of the nozzle define a stop mechanism that limits the travel of the core sampling and tapping assembly within the nozzle.

In any one or more of the embodiments described above, the pilot bit includes a plurality of rotating clips which rotate vertically and are positioned within a pilot bit cross-sectional profile when the pilot bit drills through a wall thickness of the cylindrical pipe. Furthermore, a portion of the pilot bit including the rotating clips extends through the wall thickness and the rotating clips rotate and extend outside the pilot bit cross-sectional profile such that the plurality of rotating clips engage with the core sample and remove the core sample when the core sampling and tapping assembly is retracted from the outer surface location of the cylindrical pipe.

In any one or more of the embodiments described above, the core sampling and tapping assembly further includes a secondary tap that is interchangeable with the core cutter, wherein the secondary tap is threaded onto a mandrel component attachment portion of the tapping mandrel and fixedly attached to the mandrel plate.

In any one or more of the embodiments described above, the core sampling and tapping assembly further includes a centering tool including a centering tool shaft, wherein the centering tool shaft being inserted through a cutter attachment hole extends into the mandrel shaft such that the centering tool is fixedly attached to the tapping mandrel.

In any one or more of the embodiments described above, the centering tool being disposed within an interior cavity of the secondary tap such that a portion of the centering tool extends exteriorly to the secondary tap, and wherein the centering tool engages with a core sample void formed in the cylindrical pipe by the core cutter to align the secondary tap with the outer surface location of the cylindrical pipe.

In any one or more of the embodiments described above, the centering tool includes a plurality of rotating clips, wherein the rotating clips rotate vertically and are positioned within a centering tool cross-sectional profile during insertion of the centering tool into the core sample void, and wherein a portion of the centering tool including the rotating clips extends through the core sample void the rotating clips rotate and extend outside the centering tool cross-sectional profile such that the plurality of rotating clips engage with and remove a portion of the cylindrical pipe cut by the secondary tap when the core sampling and tapping assembly is retracted from the outer surface location of the cylindrical pipe.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments herein.

DETAILED DESCRIPTION

Figure 1:
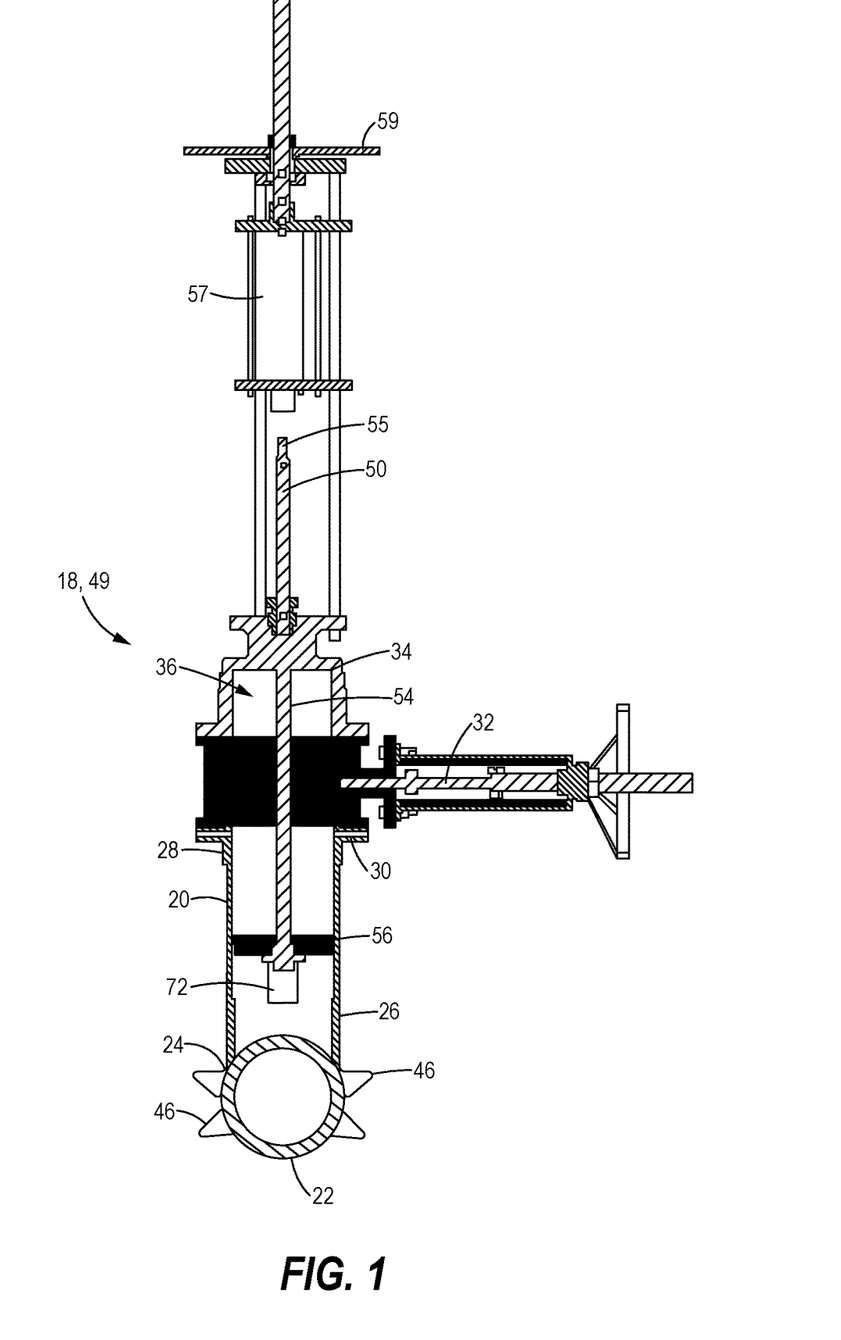
FIG. 1 is a cross sectional view of a core sampling and tapping assembly including the coring fixture and tapping machine mounted on a section of cylindrical pipe, in accordance with the present disclosure.

FIG. 1 is a cross-sectional view of a core sampling and tapping assembly 18 that includes a nozzle 20 mounted to a pressurized section of a pipe or conduit 22 such as but not limited to, a municipal water main, oil pipeline, natural gas pipeline or other such fluid conduit. In an embodiment, the nozzle 20 is attached to the section of pipe 22, or attached in close proximity to the section of pipe 22, that is in need of inspection and/or repair. Moreover, in some instances the exact size and characteristics of the pipe 22 may not be readily known. As a result, the nozzle 20 is coupled to the pipe 22 in order to conduct further inspection which helps determine characteristics such as but not limited to, the outer diameter, inner diameter, wall thickness, or other such characteristics of the pipe 22. For example, in order to install, repair, or replace a valve in the section of pipe 22 the exact dimensions (e.g., diameter and wall thickness) of the pipe 22 must first be determined. Those skilled in the art will be aware of other industrial and commercial needs for determining or confirming the unknown dimensions and other such characteristics of a pressurized pipe or conduit without depressurizing the pipe or conduit, and this disclosure in no way is limited to municipal water applications.

Still referring to FIG. 1, one embodiment of the nozzle 20 is coupled or attached to an upper saddle member 24. The upper saddle member 24 includes a hole (not shown), and a proximal end 26 of the nozzle 20 is aligned with upper saddle member 24 such that the hole is enclosed within the nozzle 20. The proximal end 26 of the nozzle 20 is welded, or otherwise attached, to the upper saddle member 24 to create a fluid tight coupling there between. Alternatively, an embodiment of the nozzle 20 is cast along with the upper saddle member 24 to form a unitary part that eliminates the need of welding, or otherwise sealingly coupling, the proximal end 26 of the nozzle 20 with the upper saddle member 24. The nozzle 20 further includes a distal end 28 including a nozzle flange 30 that is sealingly coupled or otherwise engaged with a temporary gate valve 32 inserted at the distal end 28 of the nozzle 20. Furthermore, a tap housing 34 is sealingly engaged with a top surface of the temporary gate valve 32. As a result, a sealed and enclosed interior area 36 of the core sampling and tapping assembly 18 is defined by the tap housing 34, the temporary gate valve 32, the nozzle 20 and the outer surface of the section of pipe 22.

Figure 2:
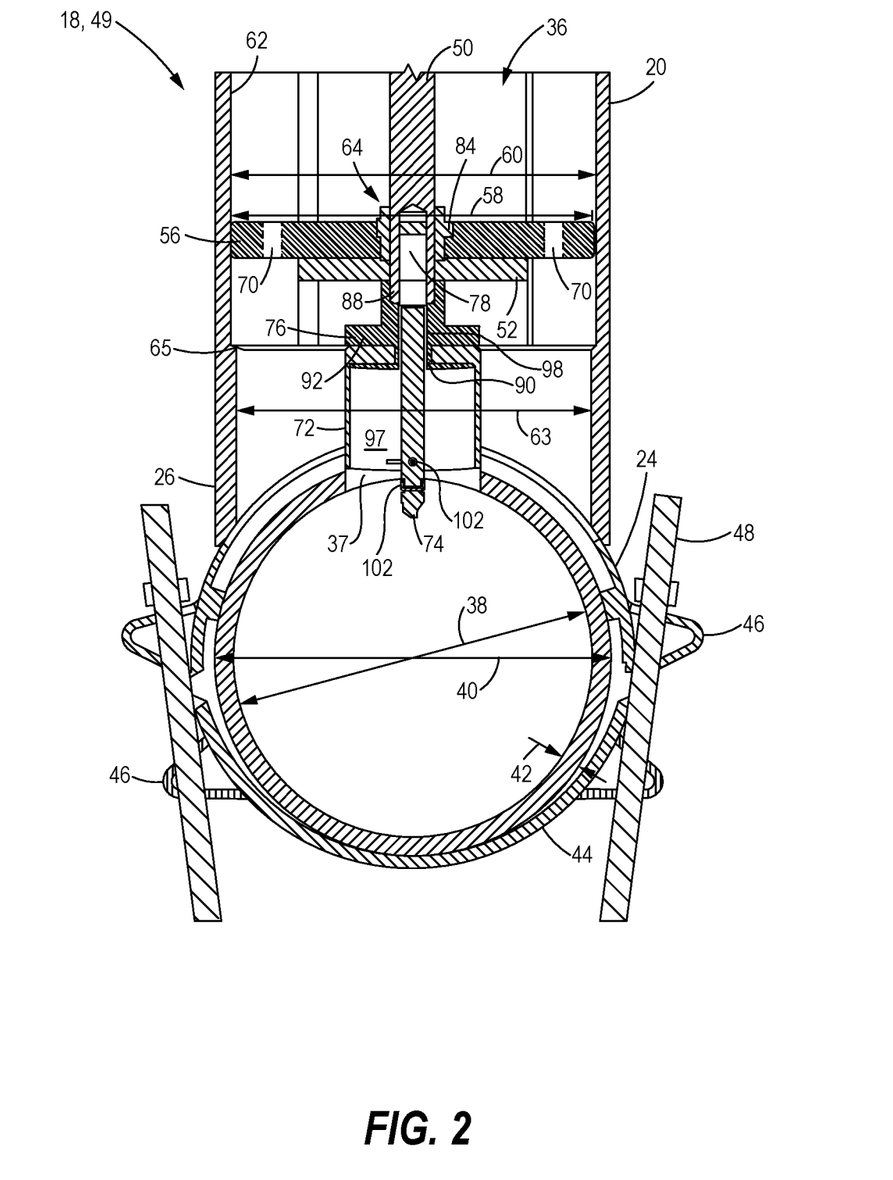
FIG. 2 is a partial cross sectional view of the core sampling and tapping assembly of FIG. 1, in accordance with the present disclosure.

As further illustrated in the exemplary embodiment of FIG. 1, the core sampling and tapping assembly 18 is configured with a core sampling fixture 49 including components such as, a tapping mandrel 50, a centering ring 56, a core cutter 72, and a pilot bit 74 (FIG. 2). As such, the tapping mandrel 50 is aligned with the tap housing 34 and the nozzle 20 and a portion of a tapping mandrel shaft 54 extends or protrudes through a sealed orifice in the top portion of the tap housing 34 and into the sealed and enclosed interior area 36 of the core sampling and tapping assembly 18. Additionally, a portion of the tapping mandrel shaft 54 extends axially exterior to the sealed orifice in the top portion of the tap housing 34. Moreover, one end of the tapping mandrel 50 includes a hex pattern 55 that is positioned exterior to the tap housing 34 and the hex pattern 55 is configured to operatively engage with a drive unit 57 such as but not limited to, an air drive unit, a hydraulic drive unit or other such drive unit.

As further illustrated in FIG. 1, an embodiment of the drive unit 57 is operably attached to a tapping machine 59 that is fixedly attached to the top portion of the tap housing 34. During operation of the core sampling and tapping assembly 18, the tapping machine 59 aligns the drive unit 57 with the hex pattern 55 of the tapping mandrel 50. Furthermore, the tapping machine 59 actuates (i.e., raise and/or lower) the drive unit 57 to engage the hex pattern 55 of the tapping mandrel 50. Additionally, the tapping machine 59 actuates (i.e., raise and/or lower) the tapping mandrel 50, the centering ring 56, the core cutter 72 and the pilot bit 74 (FIG. 2) within the sealed and enclosed interior area 36 of the core sampling and tapping assembly 18 to engage the core cutter 72 with the outer surface of the section of pipe 22. When the core cutter 72 is engaged with the outer surface of the section of pipe 22, the drive unit 57 drives the tapping mandrel 50, via the hex pattern 55, which in turn causes the core cutter 72 to rotate and cut a portion of the section of pipe 22. FIG. 1 shows an exemplary configuration of the core sampling and tapping assembly 18 including the core sampling fixture 49. However, other configurations of the core sampling and tapping assembly 18 including a post-core tapping fixture 104 (FIG. 3) are possible.

Turning to FIG. 2 with continued reference to FIG. 1, the core sampling and tapping assembly 18 is interchangeably configurable to take a core sample 37 (FIG. 2) and perform a secondary tap 114 (FIG. 3) on the section of pipe 22. As discussed above, many municipal water and other fluid distribution services have incomplete or inaccurate data for their piping and fluid conduit systems. As a result, repair and maintenance procedures on pressurized sections of pipe 22 can be difficult because of certain unknown characteristics of the pressurized section of pipe 22, such as but not limited to size, material and/or class, pipe condition and other such characteristics. Furthermore, the core sampling and tapping assembly provides alternative equipment and technology compared to using expensive, non-destructive devices to indicate pipe material, pipe size, pipe class and other such characteristics of the section of pipe 22. An additional benefit of the core sampling and tapping assembly 18 is that it allows the user to take a core sample and perform a secondary tap in a single location of the section of pipe 22.

As a result, the core sampling and tapping assembly avoids the need to use multiple tapping sleeves to create multiple holes in different sections of the pipe 22.

The determination of unknown pipe 22 geometry such as an inner diameter 38, wall thickness 42 and other internal characteristics of the pipe 22 may not easily be obtained from external inspection of the section of pipe 22. As such, one non-limiting example to determine a wall thickness 42 (i.e., outer diameter 40 minus the inner diameter 38) without needing to shut down or depressurize the pipe 22 includes positioning the nozzle 20 and the upper saddle member 24 onto the desired section of pipe 22. Moreover, in an embodiment, the upper saddle member 24 is aligned with a lower saddle member 44 positioned on a lower surface of the pipe 22. In an embodiment, the upper saddle member 24 and lower saddle member 44 each include one or more brackets 46. The upper and lower saddle members 24, 44 are aligned and are clamped to the pipe 22 by inserting one or more bolts 48 into each aligned bracket 46 to produce at least a partial seal between the upper and lower saddle members 24, 44 and the pipe 22. Moreover, the nozzle 20 is generally mounted relative to the pipe 22 such that axis of the core sampling and tapping assembly 18 is perpendicular and intersecting with the centerline axis of the section of pipe 22, as illustrated in FIG. 2.

An embodiment of the core sampling and tapping assembly 18 including the core sampling fixture 49 is further illustrated in FIGS. 1 and 2. As discussed above, the core sampling fixture 49 includes at least a portion of the tapping mandrel 50 aligned and extending into the sealed and enclosed interior area 36 of the core sampling and tapping assembly 18. Furthermore, the sealed and enclosed interior area 36 is defined between the proximal end 26 of the nozzle 20 and the tap housing 34.

Figure 6:
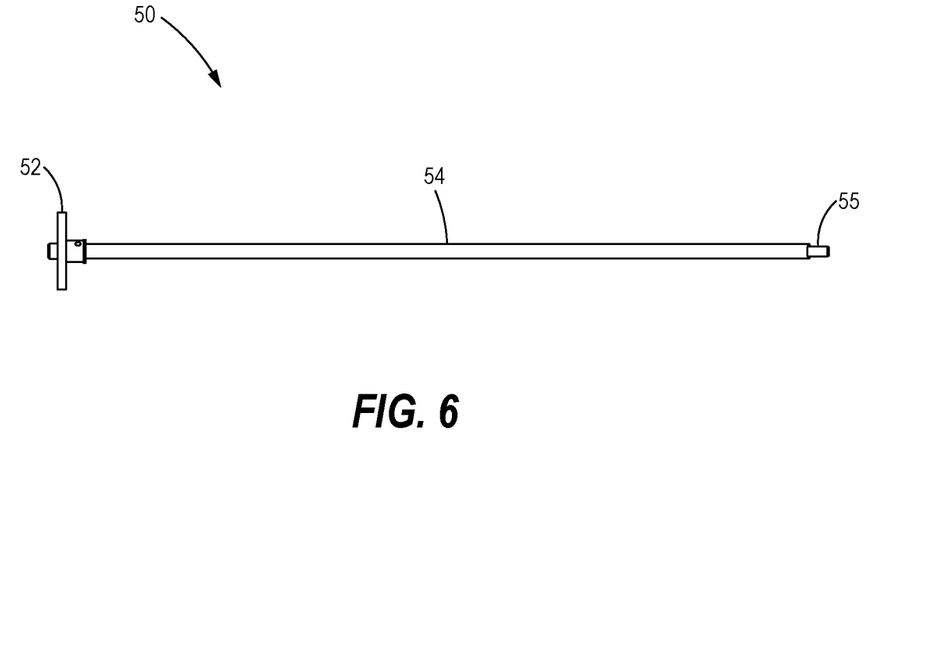
FIG. 6, a side view of a tapping mandrel incorporated into the core sampling and tapping assembly of FIGS. 1-3, in accordance with the present disclosure.

As further illustrated in FIG. 6 with continued reference to FIGS. 1 and 2, the tapping mandrel 50 includes the hex pattern 55 at one end, a mandrel plate 52 at an opposing end and a tapping mandrel shaft 54 extending there between. A portion of the tapping mandrel 50 extends into the nozzle 20 such that when fully inserted, the mandrel plate 52 is positioned adjacent to the proximal end 26 and the hex pattern 55 extends axially away from the distal end 28 of the nozzle 20 (FIG. 1). Additionally, in an embodiment, the portion of the tapping mandrel 50 including the hex pattern 55 extends externally from the sealed orifice of the tap housing 34 (FIG. 1), and the hex pattern 55 operably engages with the drive unit 57. As a result, the tapping mandrel 50 engages with the drive unit 57 and the tapping mandrel 50 is rotated, or otherwise actuated to cause a subsequent rotation of the tapping mandrel 50, the core cutter 72 and other such components of the core sampling and tapping assembly 18.

Furthermore, the core sampling fixture 49 of the core sampling and tapping assembly 18 includes a centering ring 56 which centers, or otherwise positions, the tapping mandrel 50 and other components within the sealed and enclosed interior area 36 of the core sampling and tapping assembly 18. One non-limiting example of the centering ring 56 is further illustrated in FIG. 8; the centering ring 56 is substantially circular in shape having a ring diameter 58 smaller than a distal portion inner diameter 60 of the nozzle 20. The ring diameter 58 is sized relative to the distal portion inner diameter 60 of the nozzle 20 such that the centering ring is rotatingly and slidingly engaged with an interior nozzle surface 62. Put another way, the circumference of the centering ring 56 is adjacently positioned to the interior nozzle surface 62. As a result, the centering ring 56 contacts at least a portion of the interior nozzle surface 62 and the centering ring 56 is able rotate, slide, and/or otherwise move, along the interior nozzle surface 62 between the proximal end 26 and distal end 28 (FIG. 1) of the nozzle 20.

Additionally, the interior nozzle surface 62 may include a proximal portion inner diameter 63 that is smaller than both the distal portion inner diameter 60 and the ring diameter 58 of the centering ring 56. In an embodiment, the transition between the distal portion inner diameter 60 and the proximal portion inner diameter 63 defines a stop mechanism 65 within the nozzle 20 for the core sampling fixture 49. The stop mechanism 65 prevents the centering ring 56 to from sliding along the interior nozzle surface 62 beyond the stop mechanism 65 because the ring diameter 58 of the centering ring 56 is larger than the proximal portion inner diameter 63. As a result, the distal portion inner diameter 60 and proximal portion inner diameter 63 can be configured to position the stop mechanism 65 at a location within the nozzle 20 to define an axial range of movement of the core sampling and tapping assembly 18 within the nozzle 20. Additionally, when the centering ring 56 contacts the stop mechanism 65 the interaction may send a signal to the user that the core sampling and tapping assembly 18 has reached the travel limit at the proximal end 26 and the core sampling fixture 49 has finished cutting the core sample 37 from the section of pipe 22.

Figure 7:
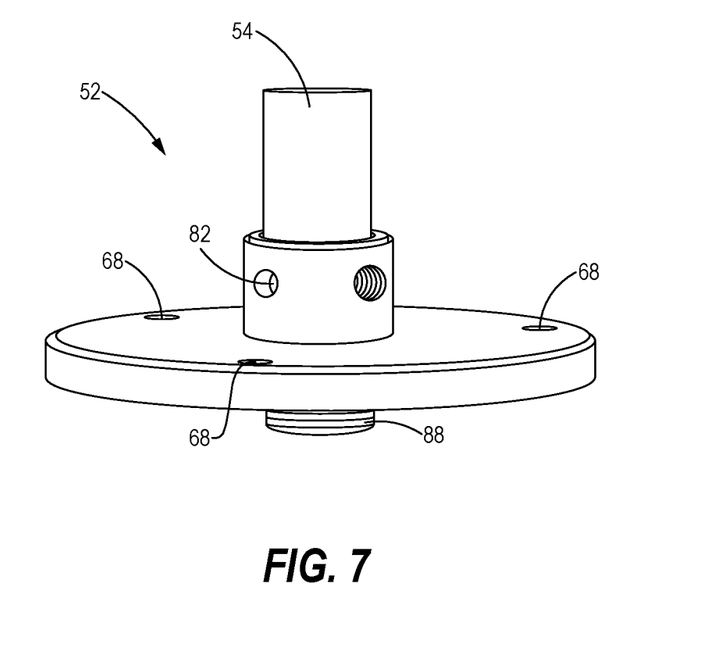
FIG. 7 a perspective view of a mandrel plate of the tapping mandrel of FIG. 6, in accordance with the present disclosure.
Figure 8:
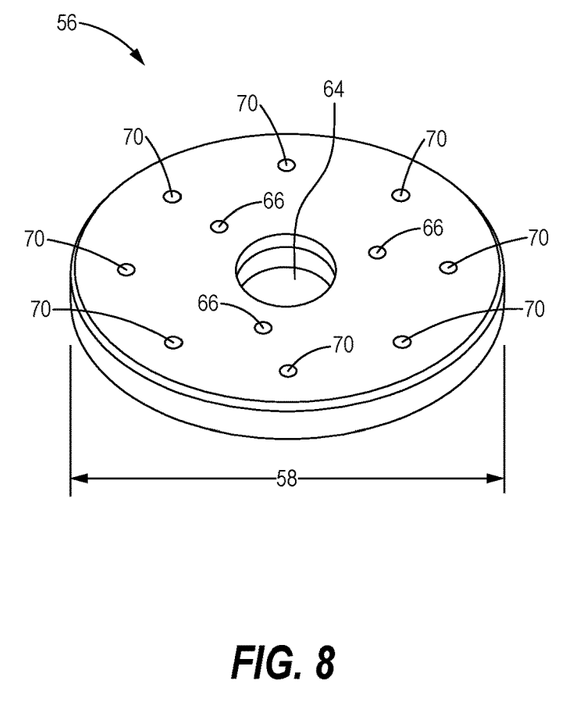
FIG. 8 is a perspective view of a centering disk incorporated into the core sampling and tapping assembly including the coring fixture of FIG. 2, in accordance with the present disclosure.

As further illustrated in FIG. 8 with continued reference to FIG. 2, an embodiment of the centering ring 56 includes a mandrel aperture 64 for mounting the centering ring 56 onto the tapping mandrel 50, and the tapping mandrel shaft 54 may be aligned with the mandrel aperture 64 such that the tapping mandrel 50 extends there through. Moreover, the centering ring 56 is positioned at the end of the tapping mandrel 50 including the mandrel plate 52. In some embodiments, the centering ring 56 is in direct contact and fixedly attached to the mandrel plate 52; however other positions of the centering ring relative to the mandrel plate 52 are possible. As a result, the centering ring 56 further includes one or more mandrel attachment holes 66 which correspond to one or more ring attachment holes 68 (FIG. 7) of the mandrel plate 52. A bolt or other such fastening device is inserted through the mandrel attachment holes 66 and the ring attachment holes 68 to fixedly attach the centering ring 56 to the mandrel plate 52.

The centering ring 56 also includes a plurality of equalization holes 70 arranged in a circular pattern and extending through the centering ring 56. The plurality of equalization holes 70 provide pressure equalization above and below the centering ring 56 during operation of the core sampling and tapping assembly 18 by allowing water, or other such fluid, to flow from one side the centering ring 56 to the other side as the core sampling and tapping assembly 18 moves between the distal end 28 (FIG. 1) and proximal end 26 of the nozzle 20. In one non-limiting example illustrated in FIG. 2, the equalization holes 70 are arranged in a circular pattern such that a diameter of the circular pattern of equalization holes 70 is larger than the diameter of the mandrel plate 52. As a result, the equalization holes 70 are positioned radially exterior to the circumference of the mandrel plate 52. However, other arrangements and positioning of the equalization holes are possible.

In an embodiment, the core sampling fixture 49 of the core sampling and tapping assembly 18 further includes a core cutter 72 and pilot bit 74 that is operatively coupled to the tapping mandrel 50 and the mandrel plate 52. Additionally, a mandrel adapter 76 may be disposed between the mandrel plate 52 and the core cutter 72. Typically, the mandrel adapter 76 is used when the core sampling fixture 49 of the core sampling and tapping assembly 18 incorporates a core cutter 72 having a size that is not compatible with the tapping mandrel 50.

Figure 9:
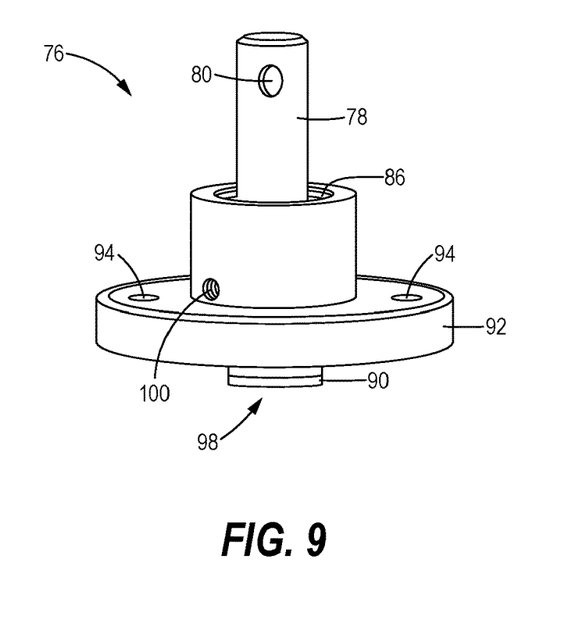
FIG. 9 is a perspective view of a mandrel adaptor incorporated into the core sampling and tapping assembly including the coring fixture of FIG. 2, in accordance with the present disclosure.

As further shown in FIG. 9, with continued reference to FIG. 2, one embodiment of the mandrel adapter 76 includes an adapter shaft 78 which is inserted into the mandrel plate 52 and a portion of the tapping mandrel shaft 54. The adapter shaft 78 includes a short slot 80, which is a hole or a slot that extends through the adapter shaft 78. The short slot 80 corresponds to a mandrel hole 82 (FIG. 7) formed through the tapping mandrel shaft 54 and mandrel plate 52. Therefore, when the adapter shaft 78 is inserted into the tapping mandrel shaft 54, the short slot 80 is aligned with the mandrel hole 82, and clevis pin 84 is inserted into the aligned short slot 80 and mandrel hole 82 to secure, or otherwise attach, the mandrel adapter 76 to the tapping mandrel 50.

Figure 4:
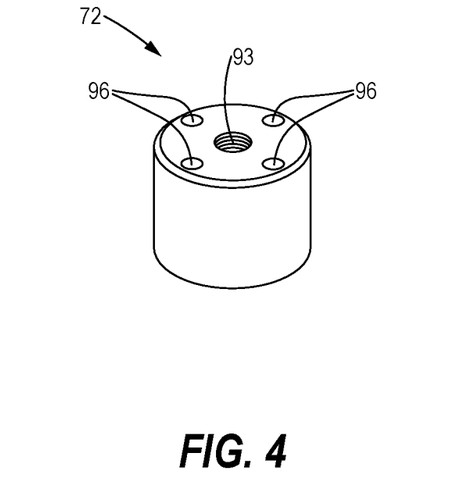
FIG. 4 is a perspective view of a core cutter used with the core sampling and tapping assembly of FIGS. 1 and 2, in accordance with the present disclosure.

The mandrel adapter 76 may further include a threaded portion 86 (FIG. 9) which correspondingly threads onto a mandrel component attachment portion 88 of the tapping mandrel 50. In the embodiment illustrated in FIG. 2, the mandrel component attachment portion 88 extends axially exterior from a bottom surface of the mandrel plate 52 and the threaded portion 86 (FIG. 9) of the mandrel adapter 76 threads onto the mandrel component attachment portion 88 to provide compatible attachment geometry between the core cutter 72 and tapping mandrel 50. For example, the mandrel adapter 76 further includes a core cutter post 90 that extends axially away from a bottom surface of an adaptor backing plate 92. The core cutter post 90 further includes threads 93 (FIG. 4) that correspondingly thread, or otherwise mate, with threads on the core cutter 72; however other methods are possible for attaching the core cutter 72 to the mandrel adapter 76. As a result, the core cutter 72 is threaded onto the core cutter post 90 and positioned in direct contact with the adaptor backing plate 92.

The mandrel adapter 76 further includes one or more adaptor attachment holes 94 (FIG. 9) that correspond to one or more cutter attachment holes 96 (FIG. 4) on the core cutter 72. In an embodiment, a bolt or other fastening device is threaded, or otherwise, inserted into each of the adaptor attachment holes 94 on the mandrel adapter 76 and cutter attachment holes 96 on the core cutter 72 to further secure the core cutter 72 to the mandrel adapter 76. Alternatively, the core cutter 72 can be directly threaded onto the mandrel component attachment portion 88 in the core sampling and tapping assembly 18 configuration which does not need or use the mandrel adapter 76.

Referring back to FIG. 2, with the core cutter 72 fixedly attached to the mandrel adapter 76, or directly attached to the tapping mandrel 50, the pilot bit 74 is centered within an interior cavity 97 of the core cutter 72 and attached to the core sampling and tapping assembly 18. In an embodiment, the mandrel adapter 76 includes a center bore 98 (FIG. 9) which accepts the pilot bit 74. The mandrel adapter 76 further includes a bit set screw hole 100 (FIG. 9) for a set screw to secure the pilot bit 74 within the center bore 98. The pilot bit 74 may further include one or more rotating clips 102 that help hold and remove the core sample 37 from the section of pipe 22.

In one non-limiting example, during operation of the core sampling and tapping assembly 18 rotation of the tapping mandrel 50 causes a corresponding rotation of the pilot bit 74 and the core cutter 72. As the pilot bit 74 comes into contact with and drills through the section of pipe 22, interaction between the rotating clips 102 and the wall of the drilled hole causes the rotating clips 102 rotate upwards into a vertical position within the profile the pilot bit 74. Once the pilot bit 74 has drilled through the wall thickness 42 of the section of pipe 22, the clips are no longer in contact with the wall of the drilled hole. Due to continued rotation of the pilot bit 74 and gravity, the rotatable clips 102 are free to rotate approximately 90 degrees such that the rotatable clips 102 extend radially exterior (i.e., orthogonal) relative to the circumference of the pilot bit 74. As a result, the rotating clips 102 contact the core sample 37 being cut into the pipe 22. Furthermore, once the core cutter 72 has completely cut through the section of pipe 22 the rotating clips 102 contact, or otherwise grab the core sample 37 to keep it from falling into the section of pipe 22. Additionally, the rotating clips 102 maintain contact with the core sample 37 and remove the core sample 37 from the section of pipe 22 as the core sampling and tapping assembly 18 is retracted from the surface of the pipe 22.

Figure 3:
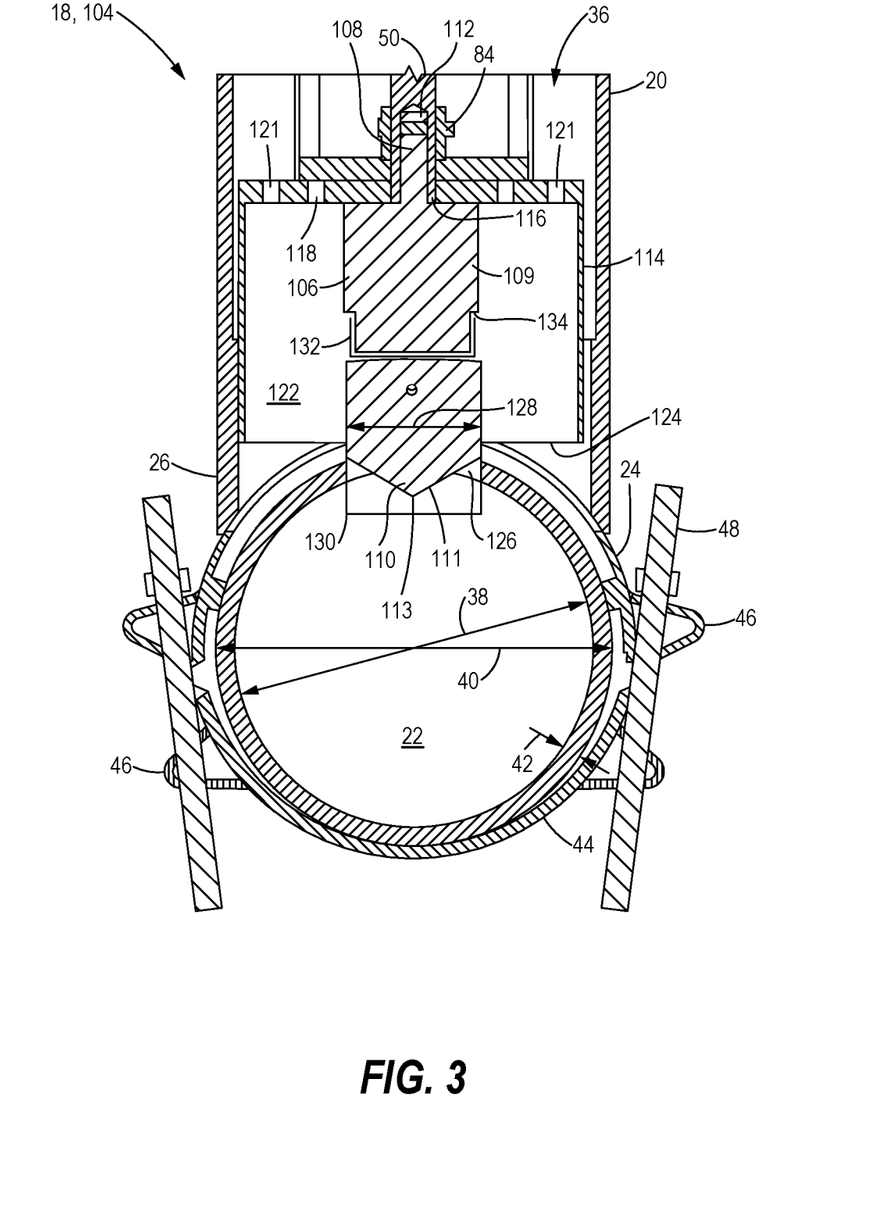
FIG. 3 is a partial cross sectional view of the core sampling and tapping assembly of FIG. 1, including the post-core tapping fixture mounted on a portion of cylindrical pipe, in accordance with the present disclosure.

Referring now to FIG. 3, the core sampling and tapping assembly 18 configured for tapping or making a secondary tap into the section of pipe 22 is illustrated. As described above, the core sample 37 (FIG. 2) is removed from the pipe 22 and used to determine unknown dimensions such as pipe inner diameter 38, wall thickness 42 and the like. Furthermore, the core sample 37 can be used to assess pipe condition by examining the core sample 37 to look for significant sediment accumulation (i.e., tuberculation) on the interior surface of the pipe 22. Additionally, the cross section of the core sample 37 can be measured to look for corrosion, deterioration, and/or reduction of the wall thickness 42 of the section of pipe 22.

Once the data and other information is collected from the core sample 37, an embodiment of the core sampling and tapping assembly 18 is converted to include the post-core tapping fixture 104 in order to continue repairs and/or valve installation to the section of pipe 22. Typically, following removal of the core sample 37, the nozzle 20, upper saddle member 24 and lower saddle member 44 are left in place. As described above, the nozzle 20 is generally mounted relative to the pipe 22 such that the core sampling and tapping assembly 18 is aligned such that the axis of the core sampling and tapping assembly 18 is perpendicular and intersecting with the centerline axis of the section of pipe 22, as illustrated in FIGS. 2-3.

The upper saddle member 24 remains aligned with the lower saddle member 44 positioned on a lower surface of the pipe 22. In an embodiment, the upper saddle member 24 and lower saddle member 44 each include one or more brackets 46. The upper and lower saddle members 24, 44 are aligned and are clamped to the pipe 22 by inserting one or more bolts 48 into each aligned bracket 46 to produce at least a partial seal between the upper and lower saddle members 24, 44 and the section of pipe 22. However, straps, clamps or other such devices can be alternatively used to secure the upper saddle member 24 and lower saddle member 44 to the pipe 22.

An embodiment of the core sampling and tapping assembly 18 including the post-core tapping fixture 104 uses several components in common with the core sampling fixture 49 illustrated in FIG. 2. For example, the post-core tapping fixture 104 of the core sampling and tapping assembly 18 includes the tapping mandrel 50. At least a portion of the tapping mandrel 50 is aligned with and extends into the sealed and enclosed interior area 36 of the core sampling and tapping assembly 18. The sealed and enclosed interior area 36 being defined between the proximal end 26 of the nozzle 22 and the tap housing 34 (FIG. 1). As further illustrated in FIG. 6 with continued reference to FIG. 3, the tapping mandrel 50 includes the hex pattern 55 at one end, the mandrel plate 52 at an opposing end and the tapping mandrel shaft 54 extending there between. A portion of the tapping mandrel 50 extends into the nozzle such that when fully inserted, the mandrel plate 52 is positioned adjacent to the proximal end 26 on the nozzle 20 and the hex pattern 55 extends axially away from the distal end 28 of the nozzle 20 (FIG. 1). Additionally, in an embodiment, the portion of the tapping mandrel 50 including the hex pattern 55 extends externally from the sealed orifice of the tap housing, and the hex pattern 55 operably engages with the drive unit 57 (FIG. 1).

An embodiment of the core sampling and tapping assembly 18 including the post-core tapping fixture 104 does not use the centering ring 56 from the core sampling fixture 49 (FIG. 2). Rather, a centering tool 106 is operatively coupled to the tapping mandrel 50 to center and position the core sampling and tapping assembly 18 including the post-core tapping fixture 104. The centering tool 106 includes a centering tool shaft 108, a tapered portion 110, and a centering tool body 109 disposed there between. In one non-limiting example, the centering tool body 109 has a substantially cylindrical shape and the centering tool shaft 108 extends axially away from one end of the centering tool body 109. Moreover, the tapered portion 110 forms a conical end at an opposing end of the centering tool body 109. In an embodiment, the tapered portion 110 includes a sloped surface 111 which meet to define a centering tool tip 113. In some embodiments, the tapered portion 110, sloped surface 111 and centering tool tip 113 interact with the outer surface of the section of pipe 22 to help center and align the post-core tapping fixture 104 with a core sample void 126 left in the section of pipe 22 by removal of the core sample 37 (FIG. 2).

Figure 10A:
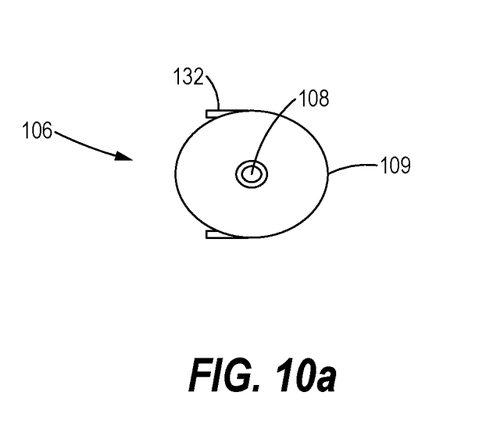
FIG. 10a is a top view of a centering tool incorporated into the core sampling and tapping assembly including the post-core tapping fixture of FIG. 3, in accordance with the present disclosure.
Figure 10B:
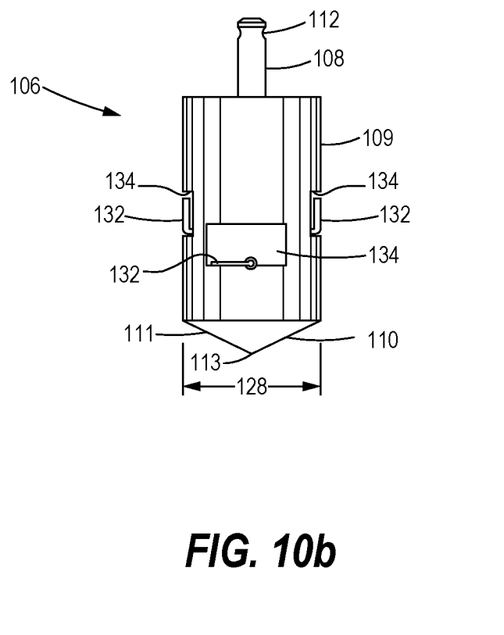
FIG. 10b is a side view of the centering tool of FIG. 10a, incorporated into the core sampling and tapping assembly including the post-core tapping fixture of FIG. 3, in accordance with the present disclosure.

As further shown in FIGS. 10a and 10b, with continued reference to FIG. 3, the centering tool 106 includes the centering tool shaft 108 with a retaining hole 112 extending there through and the retaining hole 112 corresponds to the mandrel hole 82 (FIG. 7) formed through the tapping mandrel shaft 54 and mandrel plate 52. As a result, when the centering tool shaft 108 is inserted into the proximate end of the tapping mandrel shaft 54, the retaining hole 112 of the centering tool shaft 108 is aligned with the mandrel hole 82. The clevis pin 84 is inserted into the aligned retaining hole 112 and mandrel hole 82 to secure, or otherwise attach, the centering tool 106 to the tapping mandrel 50.

Figure 5:
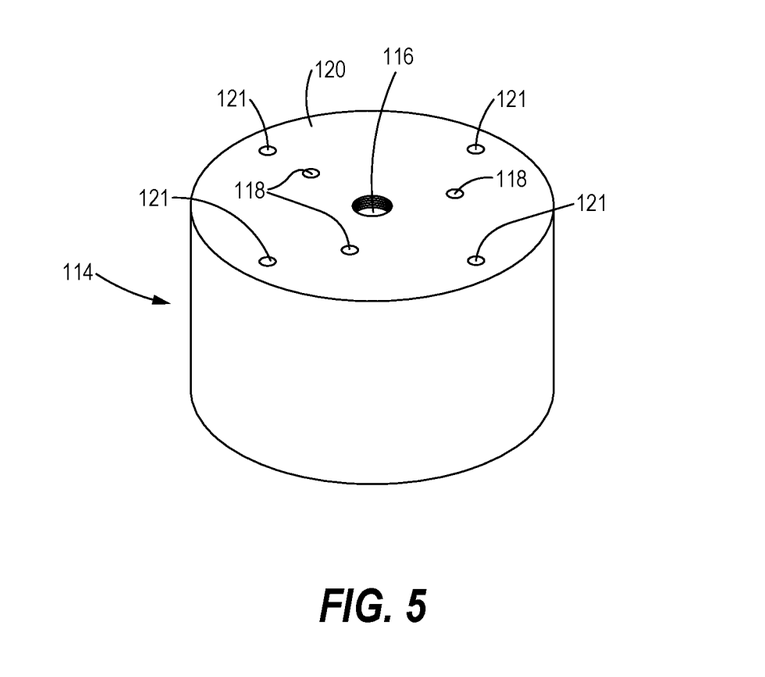
FIG. 5 is a perspective view of a secondary tap incorporated into the core sampling and tapping assembly of FIGS. 1 and 3, in accordance with the present disclosure.

Additionally, the secondary tap 114 is included in the post-core tapping fixture 104 of the core sampling and tapping assembly 18. In an embodiment, the secondary tap 114 is chosen based on the dimensions obtained from the core sample 37 (FIG. 2) removed from the section of pipe 22 and the size of the nozzle 20 attached to the section of pipe 22. Furthermore, as illustrated in FIG. 5, an embodiment of the secondary tap 114 includes a threaded cutter attachment hole 116 that corresponds, or otherwise mates, with the threads of the mandrel component attachment portion 88. As a result, the secondary tap 114 is threaded onto the tapping mandrel 50. The secondary tap 114 further includes one or more mandrel attachment holes 118 formed in a top surface 120 of the secondary tap 114. When the secondary tap 114 is threaded onto the mandrel component attachment portion 88, the top surface 120 contacts the mandrel plate 52 and the mandrel attachment holes 118 align with the ring attachment holes 68 (FIG. 7) of the mandrel plate 52. As a result, a screw, or other such fastening device is inserted into the aligned mandrel attachment holes 118 and ring attachment holes 68 to fixedly attach the secondary tap 114 to the mandrel plate 52.

An embodiment of the secondary tap 114 also includes a plurality of equalization holes 121 extending through the top surface 120. The plurality of equalization holes 121 provide pressure equalization above and below the secondary tap 114 during operation of the core sampling and tapping assembly 18 by allowing water or other such fluid to flow from one side the secondary tap 114 to the other side as the core sampling and tapping assembly 18 moves between the distal end 28 (FIG. 1) and proximal end 26 of the nozzle 20, and vice versa. In one non-limiting example illustrated in FIG. 3, the plurality of equalization holes 121 are positioned radially exterior to the circumference of the mandrel plate 52. However, other arrangements and positioning of the equalization holes are possible.

In the illustrated embodiment of FIG. 3, the centering tool 106 is positioned relative to the secondary tap 114, such that the centering tool shaft 108 is inserted through the cutter attachment hole 116 (FIG. 5) and extends into the tapping mandrel 50. As a result, the centering tool 106 is centered within an interior space 122 of the secondary tap 114. Furthermore, the centering tool 106 extends axially away from the top surface 120 of the secondary tap 114 and at least a portion of the centering tool body 109 and the tapered portion 110 protrudes exterior to a cutting end 124 of the secondary tap 114. Moreover, during operation of the core sampling and tapping assembly 18 with the post-core tapping fixture 104, the tapping machine 59 actuates the tapping mandrel 50, the centering tool 106 and the secondary tap 114 within the nozzle 20. When the post-core tapping fixture 104 is actuated towards the section of pipe 22 the tapered portion 110 of the centering tool 106, including the sloped surface 11 and centering tool tip 113, interacts with the core sample void 126 left by the removal of the core sample 37 (FIG. 2) from the section of pipe 22.

In an embodiment, a diameter 128 of the centering tool 106 is smaller than a diameter 130 of the core sample void 126 such that the tapered portion 110 guides the centering tool 106 into the core sample void 126 to align, center, or otherwise position, the secondary tap 114 with the section of pipe 22. In one non-limiting example, the diameter 128 of the centering tool 106 is sized just smaller than the diameter 130 of the core sample void 126 such that the circumference of the centering tool 106 slidingly and rotatingly engages with the circumference of the core sample void 126, to maintain concentricity of the secondary tap 114 to the nozzle 20.

As illustrated in FIG. 1, a portion of the tapping mandrel shaft 54 extends axially exterior to the sealed orifice in the top portion of the tap housing 34. Furthermore, one end of the tapping mandrel 50 includes the hex pattern 55 positioned exterior to the tap housing 34 and the hex pattern 55 is configured to operatively engage with a drive unit 57 such as but not limited to, an air drive unit, a hydraulic drive unit or other such drive unit. In an embodiment, the drive unit 57 is attached to the tapping machine 59 and the tapping machine 59 is fixedly attached to the top portion of the tap housing 34. During operation of the core sampling and tapping assembly 18, the tapping machine 59 aligns the drive unit 57 into contact with the hex pattern 55 of the tapping mandrel 50. Additionally, the tapping machine 59 may actuate (i.e., raise and/or lower) the tapping mandrel 50, the centering tool 106 and the secondary tap 114 within the sealed and enclosed interior area 36 of the core sampling and tapping assembly 18.

When the post-core tapping fixture 104 is actuated by the tapping machine 59 (FIG. 1) to lower the tapping mandrel 50, the tapered portion 110 of the centering tool 106 interacts with the core sample void 126 to align the centering tool 106 with the core sample void 126. Once properly aligned, the centering tool body 109 slidingly and rotatingly extends through the core sample void 126 and the secondary tap 114 contacts the outer surface of the section of pipe 22. As a result, the centering tool 106 is aligned and inserted into the core sample void 126 and the secondary tap 114 is engaged with the outer surface of the section of pipe 22. The drive unit 57 then drives the tapping mandrel 50, via the hex pattern 55, which in turn causes rotation of the centering tool and the secondary tap 114 such that the secondary tap 114 cuts out a portion of the section of pipe 22.

In an embodiment, the centering tool 106 includes a plurality of rotating clips 132 which allow the centering tool 106 to remove and retain the portion of the section of pipe 22 cut by the secondary tap 114. Furthermore, a clip recess 134 is formed in a portion of the cylindrical body 109 of the centering tool 106 for each of the rotating clips 132. The plurality of rotating clips 132 rotate freely within the clip recess 134. As a result, when the centering tool 106 passes through the core sample void 126 the circumference or edge of the core sample void 126 interacts with the rotating clips 132 causing them to rotate upwards into a vertical position (i.e., parallel with the centering tool shaft 108). Furthermore, when the rotating clips 132 are in the vertical position the rotating clips 132 reside within the clip recess 134 to maintain the circumferential profile of the centering tool 106 such that the centering tool 106 passes through the core sample void 126. However, once the centering tool 106 extends through the core sample void 126 and the rotating clips 132 no longer contact the circumference or edge of the core sample void 126, the rotating clips 132 rotate in approximately 90 degrees, in either direction. As a result, the rotating clips 132 protrude tangentially from the circumferential profile of the centering tool 106, as illustrated in FIG. 10a. Therefore, when the core sampling and tapping assembly 18 are finished cutting through the section of pipe 22 the rotating clips 132 extending radially from the centering tool 106 profile catch the portion of pipe 22 cut by the secondary tap 114. Furthermore, the rotating clips 132 maintain contact with newly cut portion of pipe 22 and help lift in into the nozzle 20 as the centering tool 106 and secondary tap 114 are retracted from the section of pipe 22.

INDUSTRIAL APPLICABILITY

Based on the foregoing, it can be seen that the core sampling and tapping assembly 18 may be used by service providers in the water, oil, gas, wastewater, or other such fluid distribution industries. Fluid distribution networks are often made up of a complex network of pipes and conduits that are oftentimes buried underground. In some cases, data records for the distribution networks contain incomplete or inaccurate data on pipe or conduit data, which make repairs on the distribution network more difficult. For example, when a service provider needs to replace a faulty valve, perform a hot tap or other such repair, it is helpful to know the internal diameter, wall thickness, material, and other such pipe characteristics. Exposing the outside of the pipe or conduit may indicate some pipe characteristics; however, unknown internal pipe geometries can only be determined by cutting multiple holes in the pipe, cutting out a section of the pipe for examination or by imaging or gauging equipment (e.g., ultrasonic, radiation or other such imaging technology).

As disclosed herein, the core sampling and tapping assembly 18 provides an exemplary method for determining internal pipe geometries (e.g., internal diameter, wall thickness, etc.) that is both reliable and efficient. Furthermore, the core sampling and tapping assembly 18 allows the user to avoid creating multiple holes in the pipe by performing two taps (i.e., core sample and secondary tap) in the same location and using much of the same equipment.

In general, the core sampling and tapping assembly 18 includes the nozzle 20, temporary gate valve 32, tap housing 34, tapping mandrel 50, drive unit 57 and tapping machine 59. During operation, the core sampling and tapping assembly 18 can be arranged in a variety of configurations to perform different tasks. In one non-limiting example, the core sampling and tapping assembly 18 is configured to include the core sampling fixture 49 to collect the core sample 37 from the section of pipe 22. In another non-limiting example, the core sampling and tapping assembly 18 is configured to include the post-core tapping fixture 104 to perform the secondary tap 114 on the section of pipe 22. As a result, the core sampling and tapping assembly 18 provides a flexible system for carrying out vital repairs to a pipe network. Furthermore, the flexibility of the core sampling and tapping assembly 18 allows for repair to the pipe network without the need for expensive imaging or gauging equipment (e.g., ultrasonic, radiation or other such imaging technology) or the need to create multiple holes in different areas of the network. Thus, the core sampling and tapping assembly 18 of the present application can minimize downtime and cost during repairs of the pipe network.

To collect the core sample 37 from the section of pipe 22 the core sampling and tapping assembly 18 is configured with the core sampling fixture 49. The core cutter 72 is attached to the mandrel plate 52 of the tapping mandrel 50. In some embodiments, the size of the core cutter 72 is not compatible with the tapping mandrel 50 and the mandrel adapter 76 is first attached to the mandrel plate 52. In such instances, the core cutter 72 is threaded onto the mandrel adapter 76 to fixedly attach the core cutter 72 to the mandrel plate 52 of the tapping mandrel 50. Additionally, the core sampling fixture 49 includes a pilot bit 74 that is attached to the mandrel adapter 76 and the tapping mandrel 50. The pilot bit 74 is centered within the core cutter 72 and a portion of the pilot bit 74 extends axially external to the core cutter 72. As a result, as the tapping machine 59 actuates (i.e., lowers and drives rotation) the core sampling fixture 49, the pilot bit 74 first comes into contact with the section of pipe 22 and drills a pilot hole through the wall thickness 42 of the pipe 22. Subsequently, the core cutter 72 comes into contact with the section of pipe 22 and cuts the core sample 37 from the pipe.

In one non-limiting example, the core sampling fixture 49 further includes the centering ring 56 that is attached to the tapping mandrel 50 and the centering ring 56 is sized according to a distal portion inner diameter 60 and proximal portion inner diameter 63 of the nozzle 20. In some embodiments, the proximal portion inner diameter 63 is smaller than the distal portion inner diameter 60 and a stop mechanism 65 is defined between the transition of the distal and proximal portion inner diameter 60, 63. The stop mechanism 65 creates a travel limit for the core sampling fixture 49 that limits or stops actuation of the core sampling fixture 49 when the centering ring 56 comes into contact with the stop mechanism 65.

Additionally, the centering ring 56 centers the core sampling fixture 49 within the nozzle 20 and aligns the tapping mandrel 50, core cutter 72 and pilot bit 74 such that the axis of the core sampling and tapping assembly 18 is perpendicular and intersecting with the centerline axis of the section of pipe 22. Once the coring tap is complete, the core sampling and tapping assembly 18 including the core sampling fixture 49 is retracted from the surface of the pipe 22 into the tap housing 34. The temporary gate valve 32 is closed and the tap housing 34 is removed from the distal end 28 of the nozzle 20. The core sample 37 is retrieved from the core sampling fixture 49 and examined to determine the pipe inner diameter, wall thickness and other such characteristics of the section of pipe 22.

Once the pipe data is collected the service provider can choose the appropriate secondary tap 114 to carry out the necessary repairs on the section of pipe 22. In an embodiment, the core sampling fixture 49 is interchangeable with the post-core tapping fixture 104 which includes the tapping mandrel 50 and the secondary tap 114. As such, with the temporary gate valve 32 still closed and the tap housing 34 removed from the distal end 28 of the nozzle 20, the core sampling fixture 49 is removed from the tapping mandrel 50 and the post-core tapping fixture 104 is attached to the tapping mandrel 50. The tap housing 34 is then replaced on the nozzle 20 and the temporary gate valve 32 is opened such that the core sampling and tapping assembly 18 including the post-core tapping fixture 104 can now perform the secondary tap on the section of pipe 22.

The post-core tapping fixture 104 includes the secondary tap 114 and the centering tool 106 attached to the tapping mandrel 50. The centering tool 106 is centered within the secondary tap 114 and extends axially away from the secondary tap 114 such that a portion of the centering tool 106 extends externally from the secondary tap 114. In an embodiment, the dimensions (i.e., diameter) of the centering tool 106 correspond with the dimensions (i.e., diameter) of the core cutter 72 such that the centering tool 106 fits into the core sample void 126 left in the section of pipe 22. As a result, as the tapping machine 59 actuates (i.e., lowers and drives rotation) the tapered portion 110 of the centering tool 106 first comes into contact with the core sample void 126 in the section of pipe 22. The tapered portion 110 aligns the centering tool with the core sample void 126 such that the centering tool 106 extends through the core sample void 126. As a result, the centering tool 106 aligns axis of the secondary tap 114 to be perpendicular and intersecting with the centerline axis of the section of pipe 22. Once aligned, the core sampling and tapping assembly 18 including the post-core tapping fixture 104 performs the secondary tap in the section of pipe 22.

While only certain embodiments have been set forth, alternatives and modifications will be apparent from the above description to those skilled in the art. These and other alternatives are considered equivalents and within the spirit and scope of this disclosure.

The invention claimed is:

1. A core sampling and tapping assembly for mounting to a cylindrical pipe, the core sampling and tapping assembly comprising:
    a nozzle including an interior portion extending between an open distal end and a proximal end, the proximal end of the nozzle sealingly coupled to an upper saddle member and the upper saddle member coupled to a lower saddle member for clamping the cylindrical pipe there between;
    a tapping mandrel inserted into the open distal end of the nozzle and extending through the interior portion, the tapping mandrel further including a mandrel plate attached at a first end of a mandrel shaft and a hex pattern formed at a second end of the mandrel shaft;
    a core cutter fixedly coupled to the mandrel plate;
    a pilot bit operably coupled to the mandrel plate and disposed within an interior cavity of the core cutter, wherein the tapping mandrel adjacently aligns the core cutter and the pilot bit with an outer surface location of the cylindrical pipe, and wherein the core sampling and tapping assembly rotatably drives the hex pattern of the tapping mandrel to subsequently rotate the pilot bit and core cutter to collect a core sample from the cylindrical pipe; and
    a centering ring including a ring attachment hole, wherein the mandrel shaft extends through the ring attachment hole and the centering ring is fixedly coupled to the mandrel plate.

2. The core sampling and tapping assembly of claim 1, further comprising a mandrel adaptor axially disposed between the mandrel plate and the core cutter, wherein the mandrel adaptor includes a threaded portion that correspondingly threads onto a threaded component attachment portion of the tapping mandrel such that the mandrel adaptor is fixedly coupled to the mandrel plate.

3. The core sampling and tapping assembly of claim 2, wherein the mandrel adaptor further includes a core cutter post and an adaptor bore centered within the core cutter post, and wherein the core cutter is threaded onto the core cutter post to fixedly attach the core cutter to the mandrel adaptor and the pilot bit is inserted into the adaptor bore and secured to the mandrel adaptor with a set screw.

4. The core sampling and tapping assembly of claim 1, wherein the centering ring further includes one or more equalization holes extending there through, and wherein the one or more equalization holes are positioned outside a diameter of the mandrel plate to allow fluid to travel through the centering ring as the core sampling and tapping assembly is actuated within the nozzle.

5. The core sampling and tapping assembly of claim 1, wherein the centering ring has a diameter smaller than an inner diameter of the nozzle, and wherein a circumference of the centering ring is slidingly and rotatingly engaged with an interior surface of the nozzle and wherein the centering ring centers the tapping mandrel, the core cutter and the pilot bit within the nozzle.

6. The core sampling and tapping assembly of claim 5, wherein the inner diameter of the nozzle includes a distal portion inner diameter and a proximal portion inner diameter that is smaller than the distal portion inner diameter, wherein the diameter of the centering ring is smaller than the distal portion inner diameter and larger than the proximal inner diameter of the interior portion of the nozzle, and wherein the distal portion inner diameter and the proximal inner diameter of the interior portion of the nozzle define a stop mechanism that limits the travel of the core sampling and tapping assembly within the nozzle.

7. The core sampling and tapping assembly of claim 1, further comprising a secondary tap that is interchangeable with the core cutter, wherein the secondary tap is threaded onto a mandrel component attachment portion of the tapping mandrel and fixedly attached to the mandrel plate.

8. The core sampling and tapping assembly of claim 7, further comprising a centering tool including a centering tool shaft, wherein the centering tool shaft being inserted through a cutter attachment hole extends into the mandrel shaft such that the centering tool is fixedly attached to the tapping mandrel.

9. The core sampling and tapping assembly of claim 8, wherein the centering tool being disposed within an interior cavity of the secondary tap such that a portion of the centering tool extends exteriorly to the secondary tap, and wherein a tapered portion of the centering tool engages with a core sample void formed in the cylindrical pipe by the core cutter to align the secondary tap with the outer surface location of the cylindrical pipe.

10. The core sampling and tapping assembly of claim 9, wherein the centering tool includes a plurality of rotating clips, wherein the rotating clips rotate vertically and are positioned within a centering tool cross-sectional profile during insertion of the centering tool into the core sample void, and wherein a portion of the centering tool including the rotating clips extends through the core sample void the rotating clips rotate and extend outside the centering tool cross-sectional profile such that the plurality of rotating clips engage with and remove a portion of the cylindrical pipe cut by the secondary tap when the core sampling and tapping assembly is retracted from the outer surface location of the cylindrical pipe.

11. A core sampling and tapping assembly for mounting to a cylindrical pipe, the core sampling and tapping assembly comprising:
   a nozzle including an interior portion extending between an open distal end and a proximal end, the proximal end of the nozzle sealingly coupled to an upper saddle member and the upper saddle member coupled to a lower saddle member for clamping the cylindrical pipe there between;
   a tapping mandrel inserted into the open distal end of the nozzle and extending through the interior portion, the tapping mandrel further including a mandrel plate attached at a first end of a mandrel shaft and a hex pattern formed at a second end of the mandrel shaft;
   a core cutter fixedly coupled to the mandrel plate; and
   a pilot bit operably coupled to the mandrel plate and disposed within an interior cavity of the core cutter, wherein the tapping mandrel adjacently aligns the core cutter and the pilot bit with an outer surface location of the cylindrical pipe, and wherein the core sampling and tapping assembly rotatably drives the hex pattern of the tapping mandrel to subsequently rotate the pilot bit and core cutter to collect a core sample from the cylindrical pipe;
   wherein the pilot bit includes a plurality of rotating clips which rotate vertically and are positioned within a pilot bit cross-sectional profile when the pilot bit drills through a wall thickness of the cylindrical pipe, wherein a portion of the pilot bit including the rotating clips extends through the wall thickness and the rotating clips rotate and extend outside the pilot bit cross-sectional profile such that the plurality of rotating clips engage with the core sample and remove the core sample when the core sampling and tapping assembly is retracted from the outer surface location of the cylindrical pipe.

12. A core sampling and tapping assembly for mounting to a cylindrical pipe, the core sampling and tapping assembly comprising:
   a nozzle including an interior portion extending between an open distal end and a proximal end, the proximal end of the nozzle sealingly coupled to an upper saddle member and the upper saddle member coupled to a lower saddle member for clamping the cylindrical pipe there between;
   the interior portion of the nozzle further including a distal portion having a distal portion inner diameter and a proximal portion having a proximal portion inner diameter that is smaller than the distal portion inner diameter;
   a tapping mandrel inserted into the open distal end of the nozzle and extending through the interior portion, the tapping mandrel further including a mandrel plate attached at a first end of a mandrel shaft and a hex pattern formed at a second end of the mandrel shaft; and
   a centering ring including a ring attachment hole, wherein the mandrel shaft extends through the ring attachment hole such that the centering ring is adjacently positioned and fixedly coupled to the mandrel plate.

13. The core sampling and tapping assembly of claim 12, further including a mandrel adaptor axially disposed between the mandrel plate and a core cutter, wherein the mandrel adaptor includes a threaded portion that correspondingly threads onto a threaded component attachment portion of the tapping mandrel such that the mandrel adaptor is fixedly coupled to the mandrel plate.

14. The core sampling and tapping assembly of claim 13, in which the core cutter and a pilot bit are operably coupled to the mandrel plate, wherein the mandrel adaptor includes a core cutter post and an adaptor bore centered within the core cutter post such that the core cutter threads onto the mandrel adapter to fixedly attach the core cutter to the mandrel adaptor and the pilot bit is inserted into the adaptor bore and secured to the mandrel adaptor with a set screw, and wherein the tapping mandrel adjacently aligns the core cutter and the pilot bit with an outer surface location of the cylindrical pipe such that rotation of the core cutter and pilot bit cuts a core sample into the cylindrical pipe.

15. The core sampling and tapping assembly of claim 12, wherein the centering ring includes a diameter smaller than the distal portion inner diameter and larger than the proximal inner diameter of the interior portion of the nozzle, wherein a circumference of the centering ring slidingly and rotatingly engages with an interior surface of the nozzle to center the tapping mandrel within the nozzle, and wherein the distal portion inner diameter and the proximal inner diameter of the interior portion of the nozzle define a stop mechanism that limits the travel of the core sampling and tapping assembly within the nozzle.

16. The core sampling and tapping assembly of claim 12, further comprising a secondary tap being threaded onto a component attachment portion of the tapping mandrel such that the secondary tap is fixedly coupled to the mandrel plate.

17. The core sampling and tapping assembly of claim 16, further comprising a centering tool including a centering tool shaft, wherein the centering tool shaft being inserted through a cutter attachment hole extends into the mandrel shaft such that the centering tool is fixedly attached to the tapping mandrel.

18. The core sampling and tapping assembly of claim 17, wherein the centering tool being disposed within an interior cavity of the secondary tap such that a portion of the centering tool extends exteriorly away from the secondary tap, and wherein a tapered portion of the centering tool engages with a core sample void formed in the cylindrical pipe to align the secondary tap with a centerline of the nozzle and the cylindrical pipe.

19. The core sampling and tapping assembly of claim 18, wherein the centering tool includes a plurality of rotating clips, wherein the rotating clips rotate vertically and are positioned within a centering tool cross-sectional profile during insertion of the centering tool into the core sample void, and wherein a portion of the centering tool including the rotating clips extends through the core sample void the rotating clips rotate and extend outside the centering tool cross-sectional profile such that the plurality of rotating clips engage with and remove a portion of the cylindrical pipe cut by the secondary tap when the core sampling and tapping assembly is retracted from the cylindrical pipe.

20. A core sampling and tapping assembly for mounting to a cylindrical pipe, the core sampling and tapping assembly comprising:
- a nozzle including an interior portion extending between an open distal end and a proximal end, the proximal end of the nozzle sealingly coupled to an upper saddle member and the upper saddle member coupled to a lower saddle member for clamping the cylindrical pipe there between;
- the interior portion of the nozzle further including a distal portion having a distal portion inner diameter and a proximal portion having a proximal portion inner diameter that is smaller than the distal portion inner diameter; and
- a tapping mandrel inserted into the open distal end of the nozzle and extending through the interior portion, the tapping mandrel further including a mandrel plate attached at a first end of a mandrel shaft and a hex pattern formed at a second end of the mandrel shaft;
- a mandrel adaptor axially disposed between the mandrel plate and a core cutter, wherein the mandrel adaptor includes a threaded portion that correspondingly threads onto a threaded component attachment portion of the tapping mandrel such that the mandrel adaptor is fixedly coupled to the mandrel plate;
- the core cutter and a pilot bit being operably coupled to the mandrel plate, wherein the mandrel adaptor includes a core cutter post and an adaptor bore centered within the core cutter post such that the core cutter threads onto the mandrel adapter to fixedly attach the core cutter to the mandrel adaptor and the pilot bit is inserted into the adaptor bore and secured to the mandrel adaptor with a set screw, and wherein the tapping mandrel adjacently aligns the core cutter and the pilot bit with an outer surface location of the cylindrical pipe such that rotation of the core cutter and pilot bit cuts a core sample into the cylindrical pipe; and
- wherein the pilot bit includes a plurality of rotating clips and the rotating clips rotate vertically and are positioned within a pilot bit cross-sectional profile when the pilot bit drills through a wall thickness of the cylindrical pipe, wherein a portion of the pilot bit including the rotating clips extends through the wall thickness, and the rotating clips rotate and extend outside the pilot bit cross-sectional profile such that the plurality of rotating clips engage with the core sample and remove the core sample when the core sampling and tapping assembly is retracted from the outer surface location of the cylindrical pipe.

21. A core sampling and tapping assembly for mounting to a cylindrical pipe, the core sampling and tapping assembly comprising:
- a nozzle including an interior portion extending between an open distal end and a proximal end, the proximal end of the nozzle sealingly coupled to an upper saddle member and the upper saddle member coupled to a lower saddle member for clamping the cylindrical pipe there between;
- a tapping mandrel inserted into the open distal end of the nozzle and extending through the interior portion, the tapping mandrel further including a mandrel plate attached at a first end of a mandrel shaft and a hex pattern formed at a second end of the mandrel shaft; and
- a core sampling and tapping fixture interchangeably coupled to the mandrel plate, the core sampling and tapping fixture comprising:
  - a core cutter fixedly coupled to the mandrel plate,
  - a pilot bit operably coupled to the mandrel plate and disposed within an interior cavity of the core cutter, wherein the tapping mandrel adjacently aligns the core cutter and the pilot bit with an outer surface location of the cylindrical pipe,
  - a secondary tap interchangeable with the core cutter and the secondary tap is threaded onto a component attachment portion of the tapping mandrel and fixedly attached to the mandrel plate, and
  - a centering tool including a centering tool shaft, wherein the centering tool shaft being inserted through a cutter attachment hole extends into the mandrel shaft such that the centering tool is fixedly attached to the tapping mandrel.

22. The core sampling and tapping assembly of claim 21, further comprising a mandrel adaptor axially disposed between the mandrel plate and the core cutter, wherein the mandrel adaptor includes a threaded portion that correspondingly threads onto the component attachment portion of the tapping mandrel such that the mandrel adaptor is fixedly coupled to the mandrel plate.

23. The core sampling and tapping assembly of claim 22, wherein the mandrel adaptor further includes a core cutter post and an adaptor bore centered within the core cutter post, and wherein the core cutter is threaded onto a set of post threads to fixedly attached the core cutter to the mandrel adaptor and the pilot bit is inserted into the adaptor bore and secured to the mandrel adaptor with a set screw.

24. The core sampling and tapping fixture of claim 21, further comprising a centering ring including a ring attachment hole, wherein the mandrel shaft extends through the ring attachment hole such that the centering ring is adjacently positioned and fixedly coupled to the mandrel plate.

25. The core sampling and tapping fixture of claim 24, wherein the centering ring includes a diameter smaller than a distal portion inner diameter and larger than a proximal inner diameter of the interior portion of the nozzle, wherein a circumference of the centering ring is slidingly and rotatingly engaged with an interior surface of the nozzle to center the tapping mandrel within the nozzle, and wherein the distal portion inner diameter and the proximal inner diameter of the interior portion of the nozzle define a stop mechanism that limits the travel of the core sampling and tapping assembly within the nozzle.

26. The core sampling and tapping assembly of claim 21, wherein the pilot bit includes a plurality of rotating clips and the rotating clips rotate vertically and are positioned within a pilot bit cross-sectional profile when the pilot bit drills through a wall thickness of the cylindrical pipe, wherein a portion of the pilot bit including the rotating clips extends through the wall thickness the rotating clips rotate and extend outside the pilot bit cross-sectional profile such that the plurality of rotating clips engage with and remove a core sample when the core sampling and tapping assembly is retracted from the outer surface location of the cylindrical pipe.

27. The core sampling and tapping assembly of claim 21, wherein the centering tool being disposed within an interior cavity of the secondary tap such that a portion of the centering tool extends exteriorly to the secondary tap, and wherein a tapered portion of the centering tool engages with a core sample void formed in the cylindrical pipe by the core cutter to align the secondary tap with the outer surface location of the cylindrical pipe.

28. The core sampling and tapping assembly of claim 21, wherein the centering tool includes a plurality of rotating clips, wherein the rotating clips rotate vertically and are positioned within a centering tool cross-sectional profile during insertion of the centering tool into a core sample void, and wherein a portion of the centering tool including the rotating clips extends through the core sample void the rotating clips rotate and extend outside the centering tool cross-sectional profile such that the plurality of rotating clips engage with and remove a portion of the cylindrical pipe cut by the secondary tap when the core sampling and tapping assembly is retracted from the outer surface location of the cylindrical pipe.

* * * * *